United States Patent
Chung et al.

(10) Patent No.: US 6,204,032 B1
(45) Date of Patent: Mar. 20, 2001

(54) METHOD FOR PRODUCING PRAVASTATIN PRECURSOR, ML-236B

(75) Inventors: Kae Jong Chung; Joo Kyung Lee; Joo Woong Park, all of Seoul; Dong Jin Seo, Kyungki-do; Sang Choon Lee, Seoul, all of (KR)

(73) Assignee: Yungjin Pharameutical Ind. Co., Ltd. (KR)

( * ) Notice: Subject to any disclaimer, the term of this patent is extended or adjusted under 35 U.S.C. 154(b) by 0 days.

(21) Appl. No.: 09/214,147

(22) PCT Filed: Jun. 30, 1997

(86) PCT No.: PCT/KR97/00131

§ 371 Date: Dec. 29, 1998

§ 102(e) Date: Dec. 29, 1998

(87) PCT Pub. No.: WO98/06867

PCT Pub. Date: Feb. 19, 1998

(30) Foreign Application Priority Data

Aug. 9, 1996 (KR) .................................................. 96-33249

(51) Int. Cl.$^7$ .................................................. C12P 17/06
(52) U.S. Cl. .................................................. 435/125
(58) Field of Search .................. 435/125, 136, 435/146, 254.1

(56) References Cited

U.S. PATENT DOCUMENTS

| | | | |
|---|---|---|---|
| 3,983,140 | 9/1976 | Endo et al. | 260/343.5 |
| 4,814,324 | * 3/1989 | Borris | 435/52 |
| 5,153,124 | 10/1992 | Furuya et al. | 435/125 |

FOREIGN PATENT DOCUMENTS

| | | | |
|---|---|---|---|
| 0 070 649 A2 | 7/1982 | (EP) . | |
| 547 898 A2 | 12/1992 | (EP) . | |
| 0 605 230 A1 | * 7/1994 | (EP) . | |
| 1453425 | 10/1976 | (GB) | 309/10 |

OTHER PUBLICATIONS

Patent Abstracts of Japan, vol. 17, No. 225 (C–1055), 1993, JP 4–360894 A.

A.G. Brown et al., "Crystal and Molecular Structure of Compactin, a New Antifungal Metabolite from *Penicillium brevicompactum*," J.C.S. Perkin I, 1165–1170 (1976).*

A. Endo et al., ML–236A, ML–236B, And ML–236C, New Inhibitors Of Cholesterogenesis Produced by *Penicillium citrinum*, The Journal of Antibiotics, 29:1346–1348 (Dec. 1976).*

*Biotechnology of Filamentous fungi*, Butterworth–Heinemann, Eds. D.B. Finkelstein et al., Chapter 10, P.S. Masurekar, "Therapeutic Metabolites" 241–301 (1992).*

* cited by examiner

Primary Examiner—Irene Marx
(74) Attorney, Agent, or Firm—Finnegan, Henderson, Farabow, Garrett & Dunner

(57) ABSTRACT

The present invention is related to a new method for producing ML-236B, a precursor of pravastatin sodium, in particular to a method for producing ML-236B lactone form(I), free acid form(II), sodium salt(III) shown in the formulae (I), (II), (III) by using a new microorganism isolated from soil. ML-236B is obtained from the culture broth of this microorganism and it is used as a substrate of pravastatin sodium which is a potent cholesterol-lowering agent used in treatment for hypercholesterolemia.

3 Claims, 2 Drawing Sheets

METHOD FOR PRODUCING PRAVASTATIN PRECURSOR, ML-236B

This application was filed under 35 USC 371 as the national phase PCT/KR7/00131 filed Jun. 30, 1997.

BACKGROUND OF THE INVENTION

1. Field of the invention

The present invention is related to a new method for producing ML-236B, a precursor of pravastatin sodium, in particular to a method for producing ML-236B lactone form(I), free acid form (II), and sodium salt(III) shown in the following formulae by using a new microorganism isolated from soil. ML-236B is obtained from the culture broth of this microorganism and it is used as a substrate of pravastatin sodium which is a potent cholesterol-lowering agent used in treatment for hypercholesterolemia.

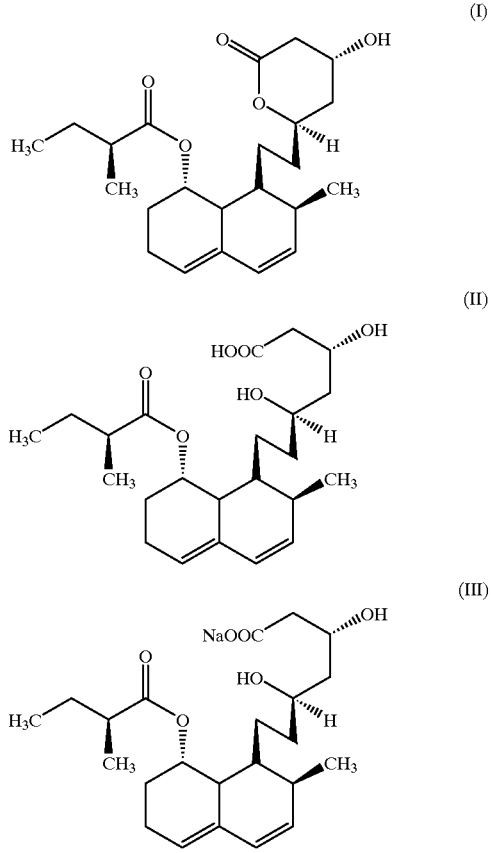

2. Description of the Prior Art

It has been known that heart disease such as myocardial infarction, arteriosclerosis have been caused mainly by hyperlipidemia, especially hypercholesterolemia. It was reported by U.S. Pat. No. 3,983,140 and UK. Patent No. 1,453,425 that a cholesterol-lowering compound called ML-236B produced by a fungus Penicillium sp. had been discovered. ML-236B is produced by soil microorganisms or chemical conversion. It was reported that *Penicillium brevicompactin*, Penicilmyces sp., *Trichoderma longibraiatum, Trichoderma pseudokoningi, Hyphomyces chrisopomus* and *Penicillium citrium* produced ML-236B (David et al., "Biotechnology of filamentous fungi", p241; JP Publication No. Pyung 4-349034).

Particularly, Sankyo Pharmaceutical Company, Japan, had developed *Penicillium citrium* SANK 18767 by mutation of a strain *Penicillium citrium* NRRL-8082 which was reported in 1971. By continuing strain development for 14 years, they had obtained *Penicillium citrium* Thom SANK 13380. ML-236B productivity had risen from 1.75 mg/l to 42.5 mg/l.

However, the method above described required so much time about 14 years to develop a strain with high ML-236B productivity. It also needed a little long cultivation time, 14 days, and showed relatively low ML-236B productivity.

SUMMARY OF THE INVENTION

To overcome the problems described above in the prior art, the present inventors have made many efforts to screen a new microorganism with higher ML-236B productivity and to develop a new method for preparing ML-236B with high yield and purity.

Finally, they isolated a new microorganism Gliocladium sp. YJ-9515 which showed very high ML-236B productivity and short cultivation time. Consequently, this strain can be used directly for industrial production of ML-236B.

DESCRIPTION OF THE DRAWINGS

The invention will be described in more detail in the drawings.

DETAILED DESCRIPTION OF THE INVENTION

Figure 1:
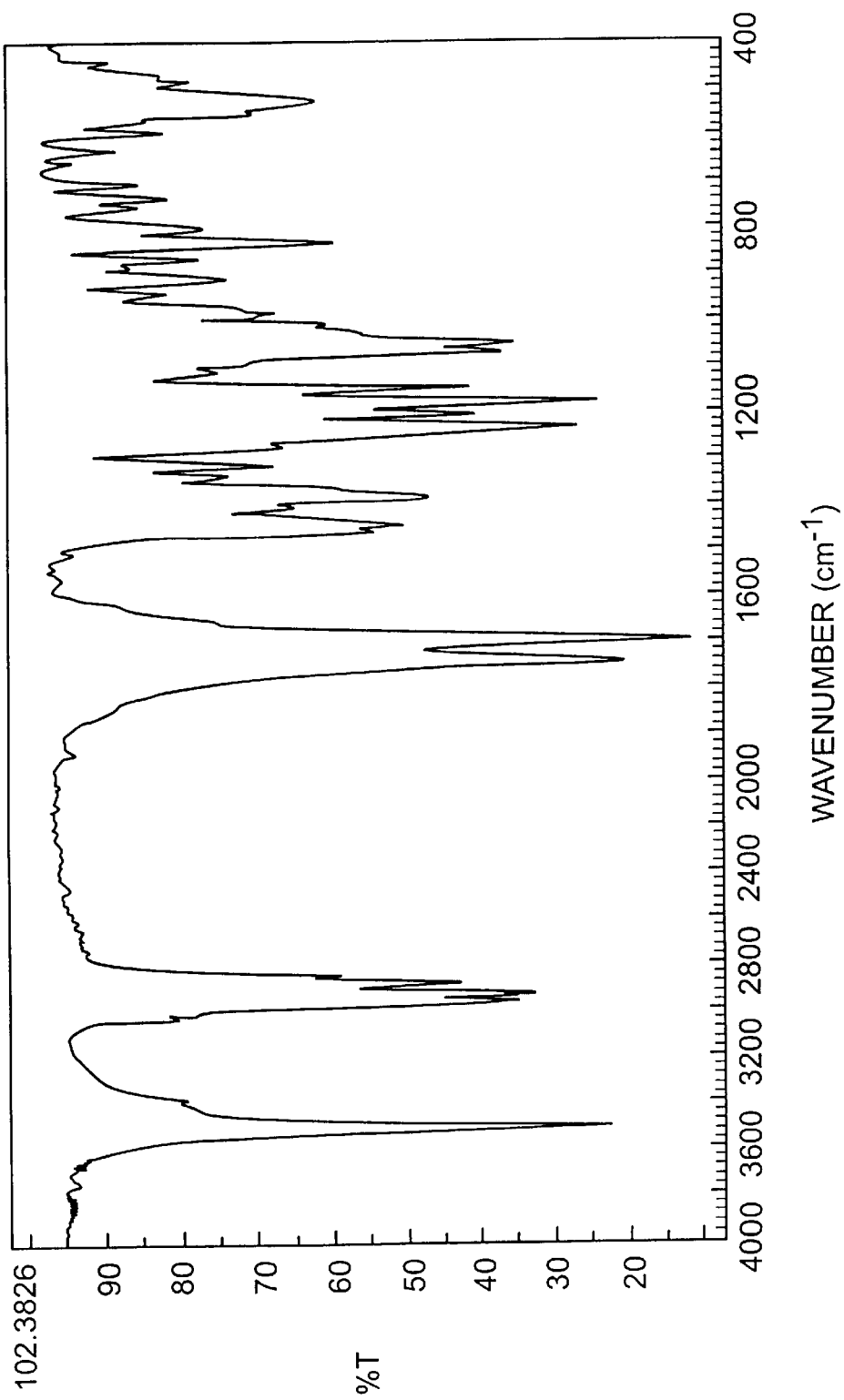
FIG. 1 is the IR spectrum of ML-236B obtained from this invention.

This invention is characterized by the fact that a new microorganism Gliocladium sp. YJ-9515(KCTC 0252BP: Accession number given by the International Depository Authority, Korea Research Institute of Bioscience and Biotechnology Korean Collection for Type Culture) is used to produce ML-236B.

More detailed description of the invention is as follows.

(A) Isolation of a New Microorganism

Soil samples diluted $10^{-3}$–$10^{-6}$ fold with water are spread on Potato-dextrose agar(PDA) and Czapak agar plate and cultured at 25° C. for 7 days. As a result, about 4,000 strains are isolated. To screen the strains which produce inhibitors of 3-hydroxy-3-methylglutaryl Coenzyme A(HMG-Co A) reductase, each strain is inoculated in 125 ml Erlenmeyer flask containing 20 ml PDA and Czapak medium and cultured. After filtering the culture broth, HMG-Co A reductase inhibition level of the filtrate and cell mass are tested.

(B) Identification of the New Microorganism

The new mircorganism obtained from above method has the following properties.

(1) Colony size of the strain, after cultured on PDA for 7 days at 25° C. is 2.0 cm in diameter, the color of colony is gray-white and surface is covered with soft, short and fuzzy aerial mycelium. Bottom of colony is bright yellow and shows narrow creases. Diffusible pigments are not produced.

(2) Colony size of the strain, after cultured on Malt-extract agar (MEA) for 7 days at 25° C. is 1.5 cm in diameter. Surface of the colony is white, soft and smooth. Bottom of the colony is bright brown and shows broad creases. Diffusible pigments are not detected.

(3) Surface of the conidiospore is rough, not branched, monoverticillated and has the protrusion.

(4) Penicillus size is 2.0–3.5 μm×1.5–3.1 μm and its surface is rough and appears long-cylindrical.

(5) Sterigma or phialide is 5.0–7.0 µm×2.0–3.0 µm in size and jar-like shaped.

(6) Conidia is 2.0–2.5 µm in size and the shape of conidia is egg-like oval.

Surface of conidia is very coarse and consists of irregular viscous aggregates.

The method used to identify the new microorganism in this invention is based on the spore formation process during the slide culture and the morphological properties. This method is generally used to identify the fungi[Dopsy et al. "The compendium of soil fungi", p859 (1980); Academy press.].

According to the results from above method, the isolated microorganism is classified as a Gliocladium species. Furthermore, the conidiospore of this strain is different in the length and morphology from other Gliocladium sp. Consequently this microorganism is approved to be a new Gliocladium sp. and named Gliocladium sp. YJ-9515 by the present inventors.

Gliocladium YJ-9515 was accepted by International Depositary Authority, Korea Research Institute of Bioscience and Biotechnology Korean Collection for Type Cultures Oun-Dong, Yusong-Ku, Taejon 305-600, Republic of Kerea, and received the accession number KCTC 0252BP on Jun. 24 1996.

For producing ML-236B using Gliocladium YJ-9515, this strain is cultured in the medium conditions in which carbon and nitrogen sources are determined according to a optimizing method. The culture medium used in this invention contains the following components with the optimal combination. Carbon sources contained in the medium are lactose glucose, glycerol, maltose, and nitrogen sources are corn steep liquor, tryptone, soy bean peptone, soy bean meal yeast extract, $NaNO_3$, and inorganic salts are $MgSO_4$, $(NH_4)_2 SO_4$, $NaH_2PO_4$.

The culture conditions are as follows.

Gliocladium YJ-9515 is cultured aerobically in shaking flasks or fermentors. Gliocladium YJ-9515 grows well in the temperature range of 10–36° C. and pH 4.0–8.0. The optimum temperature and pH range for the pravastatin precursor production are 25° C., pH 5.0–6.0, individually. For the maximum productivity of ML-236B using this strain, some kinds of medium for preserving the strain, preculture, production culture are also needed.

For the purification of ML-236B, ML-236B free acid is extracted from the culture filtrate and cell mass with ethyl acetate or methylene chloride. And the extract is concentrated in vacuo and lactonized at 30–70° C. The lactonized ML-236B is precipitated in methanol, ethanol or butyl alcohol. ML-236B is obtained as white crystal from dryness.

The physical and chemical properties of ML-236B are the same as the data reported in JP Publication No. Sho 56-12114 et al.

The present invention is represented in detail by the examples below, which aren't intended to be exemplary only.

EXAMPLE 1

Soil samples collected from all around South Korea were diluted $10^{-3}$–$10^{-6}$ fold with the sterile water in test tube. And the samples were spread on Potato-dextrose agar (PDA) and Czapak agar. The cultivation was done for 5–10 days at 25° C.

About 4,000 isolated colonies were inoculated in 125 ml Erlenmeyer flask containing 20 ml Czapak medium and cultured for 7 days at 25° C.

EXAMPLE 2

Gliocladium sp. YJ-9515(KCTC 0252BP) obtained from Example 1 was inoculated in 250 ml baffled flask containing 50 ml of a medium that comprises corn steep liquor 35 g/l, $(NH_4)_2SO_4$ 5 g/l, $MgSO_4$ 5 g/l, soybean oil 2 g/l and cultured at 180–220 rpm, 25–28° C. for 1–2 days on a rotary shaker.

Ten percent of the inoculum size of the first preculture above described was inoculated into 1,000 ml baffled flask containing 200 ml of the second preculture medium that comprises glycerol 10 g/l, maltose syrup 20 g/l, soybean peptone 30 g/l, corn steep liquor 10 g/l, $MgSO_4$ 0.5 g/l and cultured at 180–220 rpm, 25–28° C. for 1–3 days on a rotary shaker.

Ten percent of the second preculture was inoculated into the 2,000 ml baffled flask containing 400 ml of the production culture medium that comprises maltose syrup 5 g/l, tryptone 35 g/l, $CaCO_3$ 2 g/l, $(NH_4)_2SO_4$ 5 g/l, $NaH_2PO_4$ 4.5 g/l and cultured in the same condition as the first peculture.

4 days later, ten percent(v/v) of 30% glucose solution was added and cultured for more 6 days. The pH during the production culture was maintained above 5.0 with 1N ammonia solution.

Ten liter of the culture broth was centrifuged. The obtained supernatant was adjusted to pH 3.0–3.5 with 2N HCl and ML-236B was free acid-formed or lactonized.

The residual ML-236B in the cell mass was extracted with acetone or ethyl acetate, if necessary. The extract was concentrated in vacuo and added to the supernatant. ML-236B was extracted with 10 l ethyl acetate from water solution two times repeatedly and concentrated.

The residue was applied to a column of silica gel(200–300 mesh size, 200 g) in methylene chloride. From the column ML-236B was eluted with 1,000–1,500 ml methylene chloride: acetone=8:1. The ML-236B fraction was concentrated in vacuo at 50° C. to dryness. ML-236B was precipitated in 500 ml methanol at −20° C. for 24hr and filtered. Through reprecipitation, ML-236B was obtained as white crystal 8,100 mg. The obtained ML-236B was saponified into sodium salt in acetone by adding 0.2N NaOH solution slowly till pH 7.0 for about 2hr.

EXAMPLE 3

Except for using lactose instead of maltose syrup as a carbon source, Gliocladium YJ-9515 was grown in the same medium as used in Example 2. By comparison with Example 2, 24 hours of cultivation time was reduced and ML-236B productivity increased 10–20% per unit time.

Ten liter of the culture broth containing ML-236B was adjusted to pH 7.0 with 0.2N NaOH and stirred for 1–2 hr. ML-236B lactone was saponified into sodium salt form. The culture broth was centrifuged and separated into the supernatant and cell mass. The residual ML-236B in the cell mass was extracted with organic solvent and concentrated in vacuo at 40–60° C. The obtained extract was added to the supernatant. The ML-236B solution was applied to a column containing 1 l polymeric adsorbent resin HP-20(Mitsubishi chem. ind. product) and ML-236B was eluted with 2 l acetone. ML-236B fraction was concentrated in vacuo at 50° C.

The residue dissolved in 20 ml water was applied to a column of 100 g Sephadex LH-20(Sigma product) and eluted with 50% methanol solution. In another way, ML-236B was adsorbed to a column of $C_{18}$ resin(Yamazen Co. product, 200 g) and eluted with 50% acetone solution. ML-236B fraction was adjusted to pH 7.5 and concentrated in vacuo.

The concentrated fraction was dissolved in 40 ml water and adsorbed in Diaion HP-20(100 ml) and eluted with 300 ml of 50% acetone solution. ML-236B was obtained as white crystal 9,100 mg.

EXAMPLE 4

The first and second preculture were described in Example 2 above.

For the production culture, 3,050 ml medium containing tryptone 50 g, $(NH_4)_2SO_4$ 12 g, corn steep liquor 30 g and $NaH_2PO_4$ 10 g was adjusted to pH 6.0 with 1N NaOH and sterilized at 121° C. for 30 minutes. To this medium, maltose syrup 100 g in 500 ml water and $MgSO_4$ 5 g in 500 ml water sterilized separately at 121° C. for 15 minutes were added. Ten precent of the second preculture(40 ml) was inoculated and cultured.

After culturing for 3 to 4 days, one liter of 50% glucose solution was fed continuously as an additive carbon source and the final concentration of glucose in culture broth was maintained 0.05–0.2%. The pH of the culture broth was adjusted above 5.0 with 1N ammonia solution.

The cultivation was done at 150–600 rpm of agitation, more than 20% of dissolved oxygen and 0.5–1.5 vvm of aeration for 10 days. The ML-236B was purified by the same method used in Example 2 and obtained as white crystal 4,500 mg.

Comparative Example
JP No. Pyung 4-349034

The medium for the first and second seed culture contained glycerol 30 g/l, glucose 20 g/l, peptone 8 g/l, $NaNO_3$ 2 g/l, $MgSO_4$ 1 g/l. *Penicillium citrium* Thom SANK 13380 was inoculated in 500 ml round bottom flask containing 50 ml seed medium and cultured at 24° C. for 2 days.

For the production culture, five liter of tap water containing glycerine 150 g and liquid sanmalt 600 g was sterilized at 121° C. for 30 minutes. With this solution, soybean meal 300 g, peptone 150 g, Honen 300 g, gluten meal 150 g and $MgSO_4$ 15 g in 10 l water was sterilized at 121° C. for 30 minutes and mixed in 30 l fermentor.

700 ml of the second seed culture was inoculated. Ten liter of tab water containing glycerine 1,600 g, Sanmalt S 6,400 g was sterilized and fed continuously as a carbon source. The cultivation was done at 25° C., 7.5 l/min of aeration, 0.5 $kg/cm^2$ of inner pressure, 260–500 rpm of agitation, 3–5 ppm of dissolved oxygen.

For 3 to 6 days after cultivation, Sannix PP 2,000 medium 150 ml was added once a day, totally 600 ml, and the culture broth was maintained at pH 4.0 by adding the carbon source medium continuously. The concentration of reducing sugar in the culture broth was less than 1.0% and the cultivation was done for 14 days.

Forty liter of the culture broth was adjusted to pH 12 with 800 ml of 6N NaOH solution and filtered. To the filtrate was added 850 ml of 6N HCl solution until pH 5.0. ML-236B was extracted with 80 l ethyl acetate and concentrated in vacuo. 50 g ML-236 residue was obtained. The residue was dissolved in 500 ml acetonitrile and applied to a column of ODS reverse phase. ML-236B was eluted with 70% acetonitrile.

Active fractions of ML-236B were collected and concentrated in vacuo. The residue was extracted with 1.5 volume of ethyl acetate twice and concentrated in vacuo. ML-236B was precipitated in ethanol solution and obtained as white crystal 17 g.

Experimental Example

The physical properties such as appearance, melting point. molecular weight, elemental analysis, formular, UV spectrum, IR spectrum, solubility and specific rotation of ML-236B obtained from Example 2, 3 and Comparative Example are described in Table 1.

TABLE 1

| Article | EXAMPLE 2, 3 | COMPARATIVE EXAMPLE |
|---|---|---|
| Appearance | white crystal | white crystal |
| Melting point (° C.) | 150~152 | 150~152 |
| Molecular weight | calculated 390.2635 experimental 390.2392 | experimental 390.2392 |
| Elemental Analysis (%) calculated experimental | C 70.74, H 8.77, O 20.49 C 70.55 , H 8.69 C 70.85 , H 8.02 | C 70.74, O 20.49, H 8.77 |
| Formula | $C_{23}H_{34}O_5$ | $C_{23}H_{34}O_5$ |
| UV spectrum (nm, MeOH) | 230, 237, 246 | 230, 237, 246 |
| IR spectrum ($cm^{-1}$, KBr ) | 3509, 2964, 2938, 2884, 1744, 1698, 1445, 1385, 1236, 1206, 1182, 1151, 1077, 1056 | 3509, 2964, 2938, 2884, 1744, 1699, 1445, 1385, 1236, 1206, 1182, 1150, 1076, 1056 |
| Solubility soluble insoluble | methanol, chloroform, ethanol, ethyl acetate water | methanol, chloroform, ethanol, ethyl acetate water |
| Specific rotation $[\alpha]_D$ | $+283^n$ | $+283^n$ |

Figure 2:
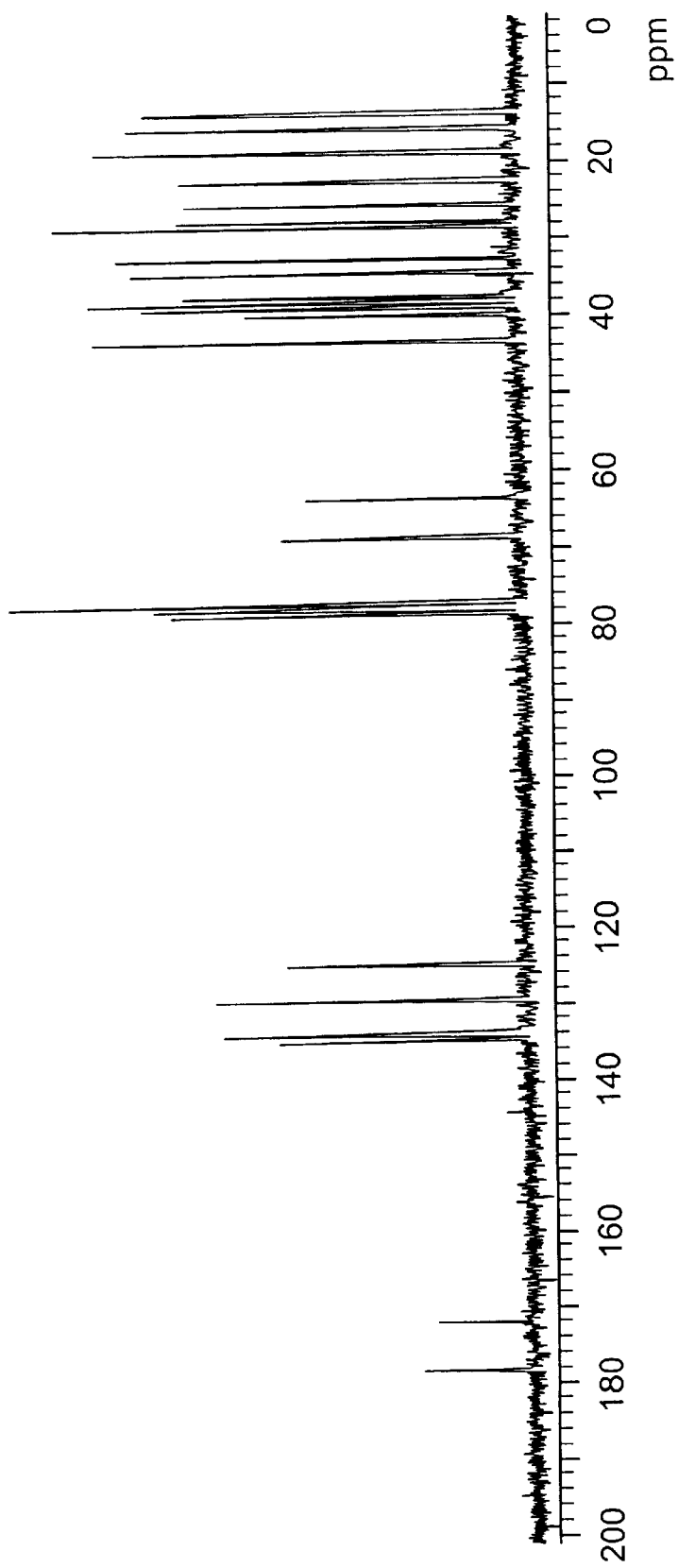
FIG. 2 is the $^{13}$C-NMR spectrum of ML-236B obtained from this invention.

$^{13}C$ NMR data of ML-236B are shown in Table 2 and FIG. 2.

TABLE 2

| The number of carbon | δ c(ppm) EXAMPLE 2,3 | δ c(ppm) COMPARATIVE EXAMPLE | The number of carbon | δ c(ppm) EXAMPLE 2,3 | δ c(ppm) COMPARATIVE EXAMPLE |
|---|---|---|---|---|---|
| C-1 | 171.50 | 170.67 | C-13 | 124.48 | 123.33 |
| C-2 | 39.31 | 38.44 | C-14 | 134.35 | 133.38 |
| C-3 | 63.18 | 62.12 | C-15 | 128.96 | 127.96 |
| C-4 | 36.88 | 35.84 | C-16 | 133.49 | 132.37 |
| C-5 | 77.22 | 76.26 | C-17 | 31.66 | 30.70 |
| C-6 | 33.75 | 32.82 | C-18 | 14.66 | 13.64 |
| C-7 | 24.83 | 23.78 | C-19 | — | — |
| C-8 | 37.66 | 36.67 | C-20 | 177.79 | 176.55 |
| C-9 | 38.31 | 37.40 | C-21 | 42.56 | 41.50 |
| C-10 | 68.45 | 67.51 | C-22 | 27.55 | 26.48 |
| C-11 | 27.06 | 26.30 | C-23 | 12.59 | 11.49 |
| C-12 | 21.74 | 20.74 | C-24 | 17.74 | 16.64 |

By using a new microorganism which was obtained from this invention, the productivity of pravastatin precursor was elevated highly and the pravastatin precursor could be prepared in a simple way in short time.

Therefore, the present invention could be used effectively in production of pravastatin precursor.

What is claimed is:

1. A method for producing at least one compound of ML-236B slected from compounds of formulae I, II, and III, comprising:

culturing, in a culture medium, Gliocladium sp. YJ-9515 having the accession number KCTC 0252 BP; and recovering said at least one compound of ML-236B; wherein the compound of formula I is the lactone form of ML-236B represented by (I)
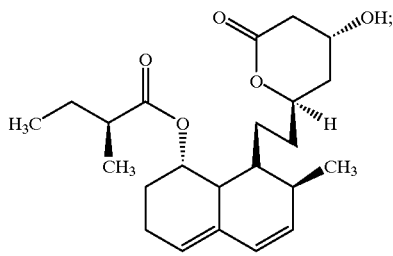
wherein the compound of formula II is the free acid form of ML-236B represented by
(II)
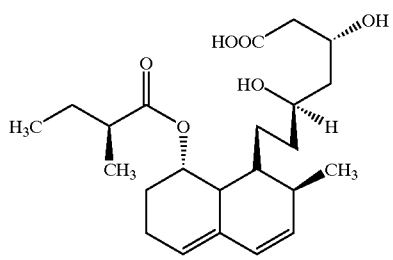
and
wherein the compound of formula III is the sodium salt form of ML-236B represented by
(III)
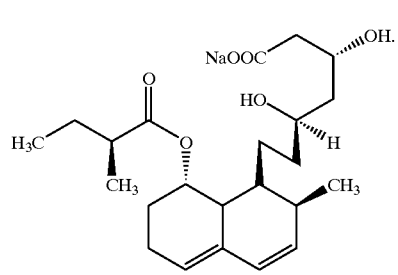
2. The method according to claim 1, wherein said culture medium comprise lactose.
3. A purified strain of Gliocladium sp. YJ-9515 (accession number KCTC 0252BP).
* * * * *

UNITED STATES PATENT AND TRADEMARK OFFICE
CERTIFICATE OF CORRECTION

PATENT NO.    : 6,204,032 B1
DATED         : March 20, 2001
INVENTOR(S)   : Kae Jong Chung et al.

It is certified that error appears in the above-identified patent and that said Letters Patent is hereby corrected as shown below:

Title page,
Item [73], "Assignee: Yungjin Pharameutical Ind., Co., Ltd." should read
-- Assignee: Yungjin Pharmaceutical Ind. Co., Ltd. --

Column 6, claim 6,
Line 59, "slected" should read -- selected --.

Signed and Sealed this

Twentieth Day of November, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO. : 6,204,032 B1  
DATED : March 20, 2001  
INVENTOR(S) : Kae Jong Chung et al.

Page 1 of 1

It is certified that error appears in the above-identified patent and that said Letters Patent is hereby corrected as shown below:

<u>Title page,</u>  
Item [73], "Assignee: Yungjin Pharameutical Ind., Co., Ltd." should read  
-- Assignee: Yungjin Pharmaceutical Ind. Co., Ltd. --

<u>Column 6, claim 1,</u>  
Line 59, "slected" should read -- selected --.

This certificate supersedes Certificate of Correction issued November 20, 2001

Signed and Sealed this

Nineteenth Day of February, 2002

Attest:

JAMES E. ROGAN  
*Attesting Officer*  *Director of the United States Patent and Trademark Office*